United States Patent [19]
Cooper

[11] Patent Number: 5,476,844
[45] Date of Patent: * Dec. 19, 1995

[54] GAMMA INULIN COMPOSITIONS

[75] Inventor: Peter D. Cooper, Monash, Australia

[73] Assignee: The Australian National University, Australian Capital Territory, Australia

[ * ] Notice: The portion of the term of this patent subsequent to Sep. 24, 2008, has been disclaimed.

[21] Appl. No.: 656,081

[22] PCT Filed: Aug. 17, 1989

[86] PCT No.: PCT/AU89/00349

§ 371 Date: Apr. 16, 1991

§ 102(e) Date: Apr. 16, 1991

[87] PCT Pub. No.: WO90/01949

PCT Pub. Date: Mar. 8, 1990

[30] Foreign Application Priority Data

Aug. 18, 1988 [AU] Australia ................................ PI9938

[51] Int. Cl.$^6$ ........................ A01N 43/04; A61K 31/715; C07H 1/00; C07G 17/00
[52] U.S. Cl. .............................. 514/55; 514/54; 514/885; 536/1.11; 536/4.1; 536/123.1; 536/124; 536/127
[58] Field of Search ................... 514/55, 26, 885, 514/54, 60, 59, 23, 57, 59, 56, 7, 47; 536/5, 4.1, 18.6, 124, 127; 435/252.1, 80; 530/387

[56] References Cited

PUBLICATIONS

Leslie et al., Chemical Abstracts 114(5):35579v (1990).

Snyderman et al., Infect Immun (Abstract), 11(2) pp. 273–279, (1975 Feb. ).

Cooper et al.; Molecular Immunology (vol. 23, No. 8); Anti–Complementary Action of Polymorphic "Solubility Forms" of Particulate Inulin; 1986.

Mino et al.; "Separation of Acetylated Inulin by Reversed–Phase High Performance Liq Chromatography"; (vol. 33, No. 8); Chemical Pharmaceutical Bulletin, 1985.

Cooper et al.; "The Anti–Melanoma Activity of Inulin In Mice"; Molecular Immuno; (vol. 23, No. 8); 1986.

Primary Examiner—Michael G. Wityshyn
Assistant Examiner—Louise N. Leary
Attorney, Agent, or Firm—Bacon & Thomas

[57] ABSTRACT

An immunoactive composition comprising particles containing inulin or an inulin derivative in the gamma polymorphic form, an antigen-binding carrier material and optionally an immune modulator such as an antigenic materials or a cytokine. The compositions provide methods for enhancing immune responses. A process for preparation of the compositions is also considered.

31 Claims, 4 Drawing Sheets

GAMMA INULIN COMPOSITIONS

This invention relates to compositions including inulin in the gamma polymorphic form, which may be used as immunoactive agents.

The properties and uses of the novel gamma polymorphic form of inulin have been described in International Patent Specification No. PCT/AU86/00311. In that specification, it is disclosed that this form of inulin may be used as an activator of the alternative pathway of complement and may be appropriate as an antitumourigenic agent. It is also disclosed in that specification that the gamma polymorphic form of inulin possesses adjuvant activity.

It has now been found that the activity of the gamma polymorphic form of inulin as an immunoactive agent such as an adjuvant may be enhanced if it is associated with an antigen-binding carrier material, and that this association provides synergistic effects.

In accordance with the present invention there is provided a composition comprising particles containing inulin or an inulin derivative in the gamma polymorphic form and an antigen-binding carrier material.

The gamma polymorphic form of inulin or an inulin derivative (hereinafter referred to as "gamma inulin") and the antigen-binding carrier material may be associated in the particles by way of electrostatic or hydrophobic interactions, covalent bonding, co-precipitation, crystallization of one component onto the other component, or by a combination thereof. Preferably, the particles are prepared by co-crystallizaton of the gamma inulin and the antigen-binding carrier material so that both of these components are contained in the same particles.

The antigen-binding carrier material may comprise any material of low solubility capable of binding proteinaceous, lipid, carbohydrate and/or other antigens. For example, the antigen-binding carrier material may be selected from metal-containing precipitates such as magnesium, calcium or aluminium phosphates, sulphates, hydroxides or hydrates thereof, organic bases such as chitin (poly N-acetylglucosamine) or deacetylated derivatives thereof or basic cellulose derivatives, or organic acids including sulphated or phosphorylated polysaccharides such as heparin, dextran or cellulose derivatives.

The antigen-binding carrier material may comprise poorly soluble particles of such materials as aluminium hydroxide (alum) gel or a hydrated salt complex thereof. Conveniently, particles of the antigen-binding carrier material are smaller than 5 µm and more preferably smaller than 1–5 µm. Most preferably, the particles are 50–2000 nanometers in diameter. It is particularly favoured to have an antigen-binding carrier material which is endotoxin- and pyrogen-free, and which is pharmaceutically acceptable. Advantageously, the antigen-binding carrier material does not tend to aggregate or is treated to avoid aggregation.

In accordance with another aspect of the invention there is provided a process for the production of a composition of the invention as broadly described above, the process comprising the steps:

of providing a suspension of an antigen-binding carrier material; and (i) admixing said suspension with inulin or an inulin derivative, and thereafter converting the inulin or inulin derivative to the gamma polymorphic form; or (ii) admixing said suspension with inulin or an inulin derivative in the gamma polymorphic form;

to effect association of the inulin or inulin derivative in the gamma polymorphic form with said antigen-binding carrier material.

Preferably, a suspension of fine particles of the antigen-binding carrier material is added to a solution of inulin or inulin derivative to give a controlled ratio of gamma inulin to antigen-binding carrier material of, for instance 200:1 to 1:1 and more suitably 50:1 to 5:1 (w/w). The inulin concentration is conveniently kept above 5% w/v. An initial 6–7% w/v solution of inulin is convenient.

The resulting suspension may be rapidly cooled to a temperature such as 5° C. and stirred at such a temperature for several days to crystallize the inulin, prior to several days at 37° C. to encourage transformation of the inulin to the gamma configuration, and subsequent washing and removal of large particles.

Alternatively, it may be desirable to precipitate or otherwise intimately associate particles of inulin which are already in the gamma polymorphic configuration onto the antigen-binding carrier material, or to precipitate the antigen-binding carrier material onto particles of inulin either before or after its conversion to the gamma configuration.

As mentioned above, it is particularly desirable to employ pyrogen- and endotoxin-free solutions or suspensions of the inulin and antigen-binding carrier material fractions. Depending on the antigen-binding carrier material employed, it may also be desirable to employ reaction conditions to minimise its aggregation. For instance, when alum is employed as an antigen-binding carrier material, it may be appropriate to avoid the utilization of ammonia or $CO_2$-containing water in preparing inulin or alum solutions and to preadsorb inulin solutions with an alum gel suspension which suspension is subsequently discarded.

The inulin fraction used in the invention will typically be prepared by the processes disclosed International Patent Specification No. PCT/AU86/00311 which is hereby incorporated by reference, although as mentioned above it is desirable to avoid reagents or reaction conditions which may cause Accordingly, it is preferred that ammonia is omitted in the preparation of inulin if alum gel is to be employed as the antigen-binding carrier material.

Broadly speaking, the gamma inulin in the composition will have a molecular weight greater than about 3000, and more preferably above 8000. Its molecular weight is advantageously in the range from 8000 to about 16000 and it will be virtually insoluble in water at 37° C. after conversion to the gamma form.

Inulin derivatives envisaged for use in the composition of this invention include derivatives of β-D-[ 2-1]polyfructofuranosyl α-D glucose such as those obtained by enzymatic removal of the end glucose from inulin, for example by using an invertase or inulase enzyme. Other derivatives may include inulin in which the free hydroxyl groups have been etherified or esterified, for example by chemical substitution with alkyl, aryl or acyl groups by known methods.

The composition of the present invention produces a potentiated immune response, when compared with gamma inulin or the antigen-binding carrier material alone. This potentiated immune response was not expected. The compositions of the invention may therefore be used as adjuvants, such as in vaccine preparations, or as immunostimulants in the same way as described in Specification No. PCT/AU86/00311, incorporated herein by reference.

Thus, in another aspect this invention provides an immunotherapeutic composition which comprises as an active component thereof particles containing inulin or an inulin derivative in gamma polymorphic form and an antigen-binding carrier material, and a pharmaceutically acceptable diluent or carrier.

Any antigen or combination of antigens, such as one or more viral, bacterial, fungal or protozoal proteins, may be adsorbed onto the composition of the invention, and formulated into a vaccine preparation in association with acceptable carriers or excipients. The composition of the invention has a strong adsorptive capacity for proteins in solution, but, unlike antigen-binding carriers such as alum gel, is not aggregated by them.

In a further aspect of the invention, there is provided a vaccine composition comprising inulin or an inulin derivative particles containing in the gamma polymorphic form and an antigen-binding carrier material, and one or more antigens adsorbed thereon, together with a pharmaceutically acceptable carrier or diluent.

The invention will now be illustrated with reference to the accompanying drawings and the following non-limiting Examples.

EXAMPLE 1

Figure 1A:
FIG. 1A is an electron microscopy of the particles of the hybrid preparation of the present invention "Algammulin".

Preparation of a composition containing gamma inulin with alum as the antigen-binding carrier.

Aluminium hydroxide ("alum gel") is prepared by adjustment of a solution of the purest available aluminium chloride or sulphate with a solution of analytical grade sodium hydroxide to pH 4 to 10, preferably ca 7.0, under the conditions that yield very small particles of alum gel. The first precipitate, say up to pH 4, can be discarded to remove pyrogens and substances that may cause alum to aggregate. The second suspension is then washed by centrifugation or settling with pyrogen-free water to remove soluble matter. Excess supernatant is removed after settling overnight and the concentrated suspension sterilised by autoclaving. The weight/ml of the alum gel is calculated from assays of $Al^{3+}$ by standard chelometric or mass spectrometric methods. All solutions are preferably made up in $CO_2$-free water to minimise alum aggregation, and $CO_2$ is excluded from the process. Water can be kept over the alum gel. Inulin solutions are prepared as described in International Patent Specification No. PCT/AU86/00311, except that the crude inulin is dissolved to 8–10% w/v in water at 75° C. that has recently been boiled to remove $CO_2$ and ammonia solution is omitted. The solution is briefly slurried with 1% v/v of the prepared alum gel suspension to remove gross impurities and the alum removed by filtration or sedimentation. The inulin may be cooled and filtered as described in Specification No. PCT/AU86/00311 through DEAE-cellulose and Amberlite sulphonic acid resin (omitting ammonia), or repeatedly slurried with alum gel until free of impurities. In the former case, the solution is given a final treatment with alum gel after the Amberlite filtration and before the Zetapor filtration that ensures sterility and endotoxin removal. Subsequently the preparation is kept sterile and endotoxin-free. Inulin concentrations should now be 6–7% w/v. A fine suspension of alum gel particles (as prepared above, or "Alhydrogel" or other endotoxin-free preparation, sterilised by autoclaving) is then added to give a known w/w ratio of inulin:alum in the suggested range of 200:1 to 1:1, preferably 50:1 to 5:1 (w/w), keeping the inulin concentration greater than 5.0% w/v. The suspension is rapidly cooled to 5° C. and stirred as before, i.e. at 5° C. for several days to crystallize, transferred to 37° C. for several days to transform to the gamma configuration, then centrifuged and resuspended in water, heated for 1 hour at 50°–52° C., and washed to zero supernatant refractive index. It may be necessary to differentially centrifuge or otherwise fractionate the final suspension to remove particles greater than 1.5 μm diameter, as judged by haemocytometer observation. Alternatively, the preparation may be disrupted by sonication treatment, especially after heat treatment for example for an hour at 45°–55° C. (conveniently at 50°–52° C.) to make the particles more fragile, to create particles of a convenient size, for example in the range of 50 to 1000 nanometers in diameter. The fine suspension is adjusted to 5% w/v inulin in 0.8% NaCl plus a compatible preservative, for example 20 μg/ml phenylmercuric nitrate. The resulting composition (also referred to as a gamma inulin/alum hybrid preparation or as "Algammulin") is checked for dissolved matter, insolubility, endotoxin content, sterility and complement activation as described in Specification No. PCT/AU86/00311. In the process described above, the inulin appears to crystallize around the alum particles forming a porous capsule, and is then readily converted in situ to the gamma form. Like alum gel, the particles have a strong adsorptive capacity for proteins in solution, but unlike alum gel are not aggregated by them.

EXAMPLE 2

Protein adsorptive capacity.

40 μl of saline alone, a suspension of gamma inulin (g-IN)/alum hybrid preparation at 50 mg g-IN/ml, or suspensions containing the same quantities of g-IN or alum alone or in mixture, were mixed with 10 μl of saline containing 0.65 μg keyhole limpet haemocyanin labelled with $10^5$ cpm of $^{125}I$ and allowed to adsorb for 15 min at 23° C. The suspensions were then each mixed with 1 ml of saline of which 20 μl portions were layered in 600 μl Percoll colloid (density 1.126 g/ml) in plastic tubes of 6.5 mm internal diameter, forming a column of liquid 3 cm deep. The remainder of the suspensions were centrifuged and washed to show that the hybrid preparation and the alum suspensions had adsorbed greater than 95% of the label, while the g-IN had adsorbed less than 5% of the label. The Percoll tubes were centrifuged at 700 g for 4 minutes and processed immediately. In the tubes containing free g-IN (with or without admixed alum) or the hybrid preparation the bulk of the turbidity, representing the g-IN, remained in the top 50 μl, while in the tubes containing free alum gel all of the gel could be seen to be in or near the pellet. In the tube containing the hybrid preparation there was no visible pellet. The tubes were then fractionated by removal to replicate tubes of the top 50 μl and the next 500 μl, while the pellet (lowest 50 μl) was left in the tube. All the tubes were then counted in a gamma counter and the proportion of label in each fraction determined, as exemplified in the following table:

|  | % of $^{125}$I label | |
| --- | --- | --- |
|  | hybrid prep.* | alum gel alone |
| top 50 μl | 82.9 | 9.7 |
| middle 500 μl | 14.4 | 45.2 |
| pellet 50 μl | 2.6 | 45.1 |

*g-IN:alum ratio 12.5:1.

In the samples containing saline or g-IN alone, greater than 95% of the label remained in the top fraction. The distribution of label in the sample containing alum mixed with g-IN was the same as in the sample containing alum gel alone.

This type of experiment shows that the adsorptive capacity of the hybrid preparation is firmly associated with the gamma inulin and is distinct in sedimentation properties from free alum gel.

EXAMPLE 3

Proof of conjugation of alum and gamma inulin by electron microscopy.

Figure 1B:
FIG. 1B is an electron microscopy of gamma inulin particles.

Electron microscopy of gamma inulin particles reveals fairly uniform ovoids ca 1×1.5 microns in diameter that are difficult to visualise (FIG. 1B) unless prestained with an electron-dense substance, e.g. phosphotungstate. In contrast, electron microscopy of the particles of the hybrid preparation "Algammulin" (FIG. 1A) reveals similar-sized ovoids that are intrinsically electron-dense, i.e. are clearly visible without staining. This demonstrates that the alum and the gamma inulin are indeed contained in the same particle, and that the electron-dense alum is contained within and dispersed through the "Algammulin" particles.

EXAMPLE 4

Adjuvant effects of gamma inulin/alum hybrid preparations (Algammulin) in comparison with either component alone or in simple mixture.

When the hybrid preparation "Algammulin" prepared as described in Example 2 and carrying an adsorbed antigen (for example, keyhole limpet haemocyanin, KLH) is injected into mice, the antibody response (in terms of μg KLH-specific IgG/ml of serum) is increased several-fold over that produced in mice injected in parallel with the same antigen adsorbed on alum gel or mixed with g-IN, or adsorbed to alum gel and mixed with g-IN. In each case the g-IN and alum contents are equivalent by weight.

Figure 2A:
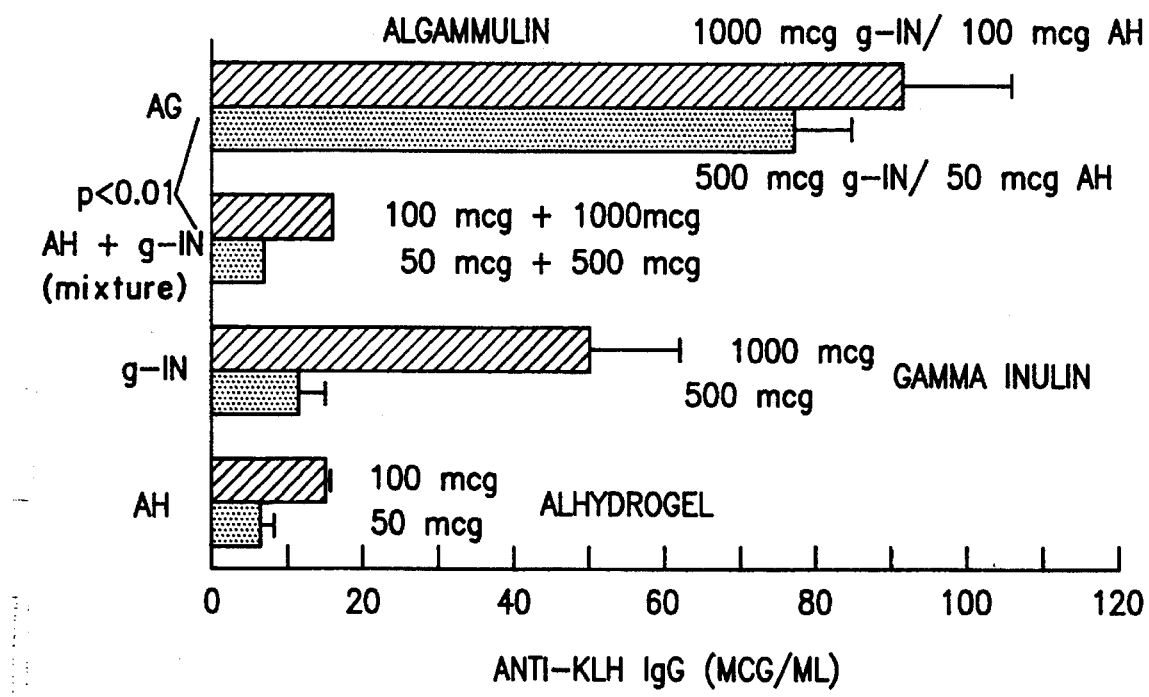
FIG. 2A shows illustrative results and standard errors with respect to "Algammulin".

BALB/c female mice were injected intraperitoneally (j.p.) in groups of 7 or 8 with 0.2 ml of endotoxin-free saline containing KLH either adsorbed to the hybrid preparation "Algammulin" or to alum gel, or mixed with g-IN, or adsorbed to alum gel and mixed with g-IN. The dose of g-IN, whether in free or hybrid form, was always 1000 μg/mouse. The mice were injected 14 days later i.p. with KLM in the absence of any adjuvant, and serum was taken after a fur%her 7 days. KLH-specific IgG/ml was measured by ELISA on sera of individual mice, and the geometric mean titre calculated. Probabilities were assessed on geometric mean titres by Mann-Whitney non-parametric ranking test and on arithmetic means of replicate geometric mean titres by Student t tests. FIG. 2A shows illustrative results and standard errors demonstrating that "Algammulin" gave specific serum antibody titres that were significantly 5.7–8.7 fold higher than a simple mixture of the same doses of alum and gamma inulin, and similarly greater than the same doses of either component alone. This experiment proves the concept that a gamma inulin/alum hybrid preparation is advantageous as a vaccine adjuvant in comparison with either component alone or in mixture, and shows that conjugation of a given dose of alum with gamma inulin greatly enhances the effect of that amount of alum by a synergistic mechanism. These tests used very low doses of KLH (1 mcg/mouse j.p.) that were barely able to elicit a seropositive response on their own, and therefore mimic a conventional "poor antigen" such as may be found in a commercial vaccine.

EXAMPLE 5

Comparison of the adjuvant effect of high doses of Algammulin with those of Freund's Adjuvants.

Figure 2B:
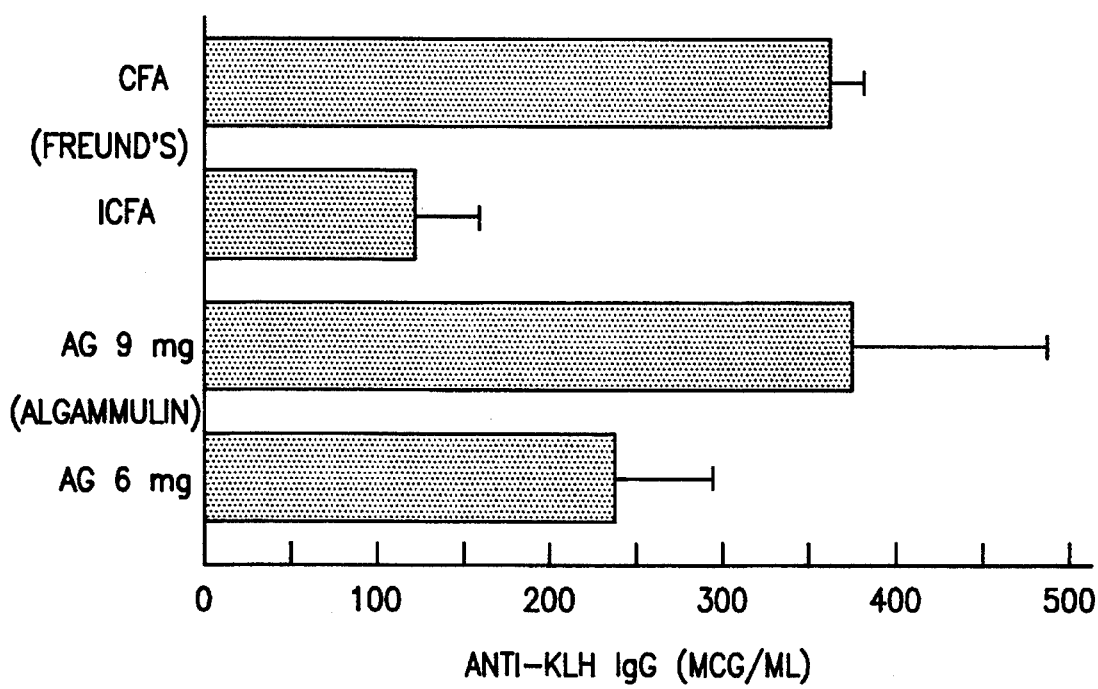
FIG. 2B shows the results of several replicated comparisons of "Algammulin" with Freunds' complete adjuvant CFA and Freund's incomplete adjuvant ICFA.

Freund's incomplete adjuvant (ICFA, a water-in-oil emulsion of antigen) and Freund's complete adjuvant (CFA, as for ICFA but with admixture of heat-killed tubercle bacilli) are recognised as standard powerful adjuvants, although too toxic for clinical application. CFA is more powerful than ICFA. FIG. 2B shows the results of several replicate comparisons of Algammulin with CFA and ICFA, using a protocol similar to that of Example 4. They demonstrate that 6 mg and 9 mg Algammulin/mouse give specific serum antibody titres that are significantly greater than those from ICFA and comparable to those from CFA.

EXAMPLE 6

Comparison of the adjuvant effect of a wide range of Algammulin doses with equivalent doses of alum alone.

Figure 3A:
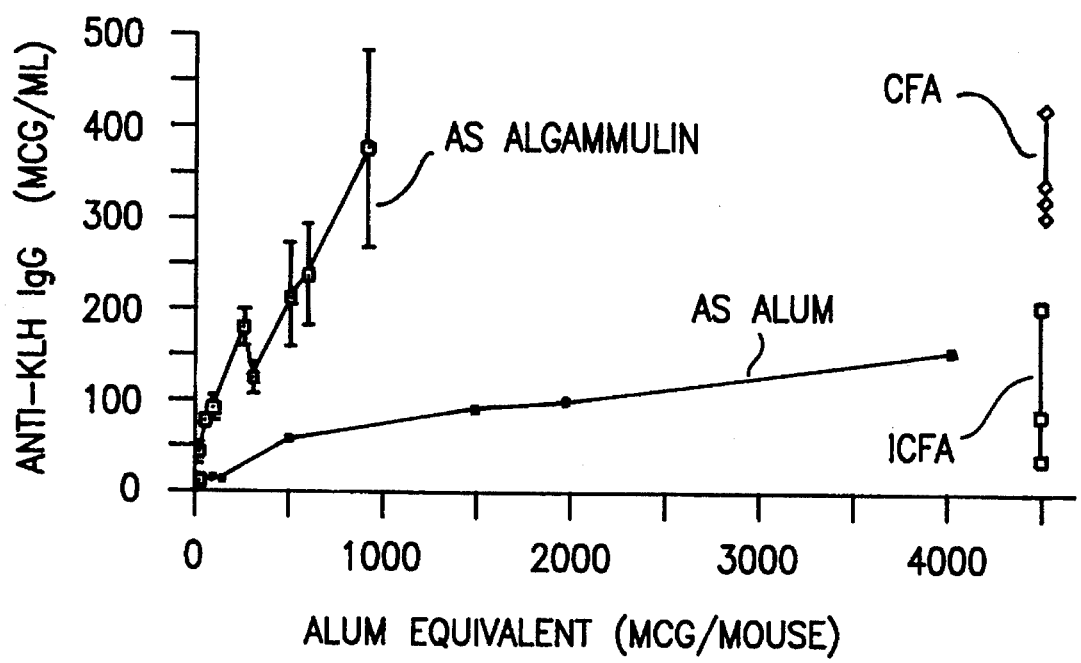
FIG. 3A shows the adjuvant effect of gamma innulin/alum hybrid, "Algammulin", and alum alone.
Figure 3B:
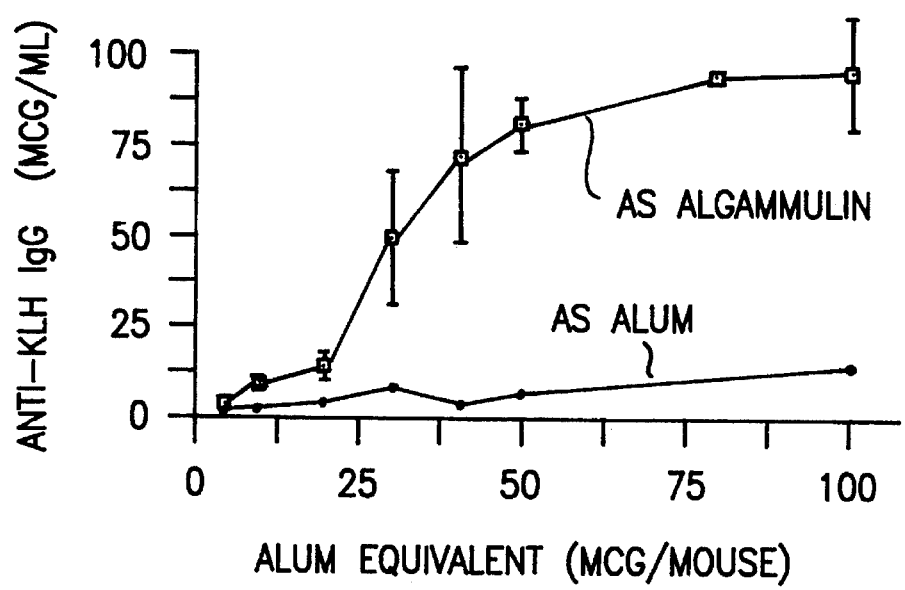
FIG. 3B shows that a given dose of alum conjugated as "Algammulin" gives specific serum antibody titers that are much greater than the same dose of alum alone.

FIG. 3 is a summary of a substantial number of replicate tests using the protocol of Example 4 and including doses of Algammulin that can be expected to fall within a physiologically acceptable range. FIG. 3B shows that a given dose of alum conjugated as Algammulin gives specific serum antibody titres that are 6.4–12.6 fold greater than the same dose of alum alone, again demonstrating the synergistic effect of conjugation with gamma inulin.

EXAMPLE 7

Comparison of the seroconversion enhancement abilities of algammulin with equivalent doses of alum alone.

Figure 4:
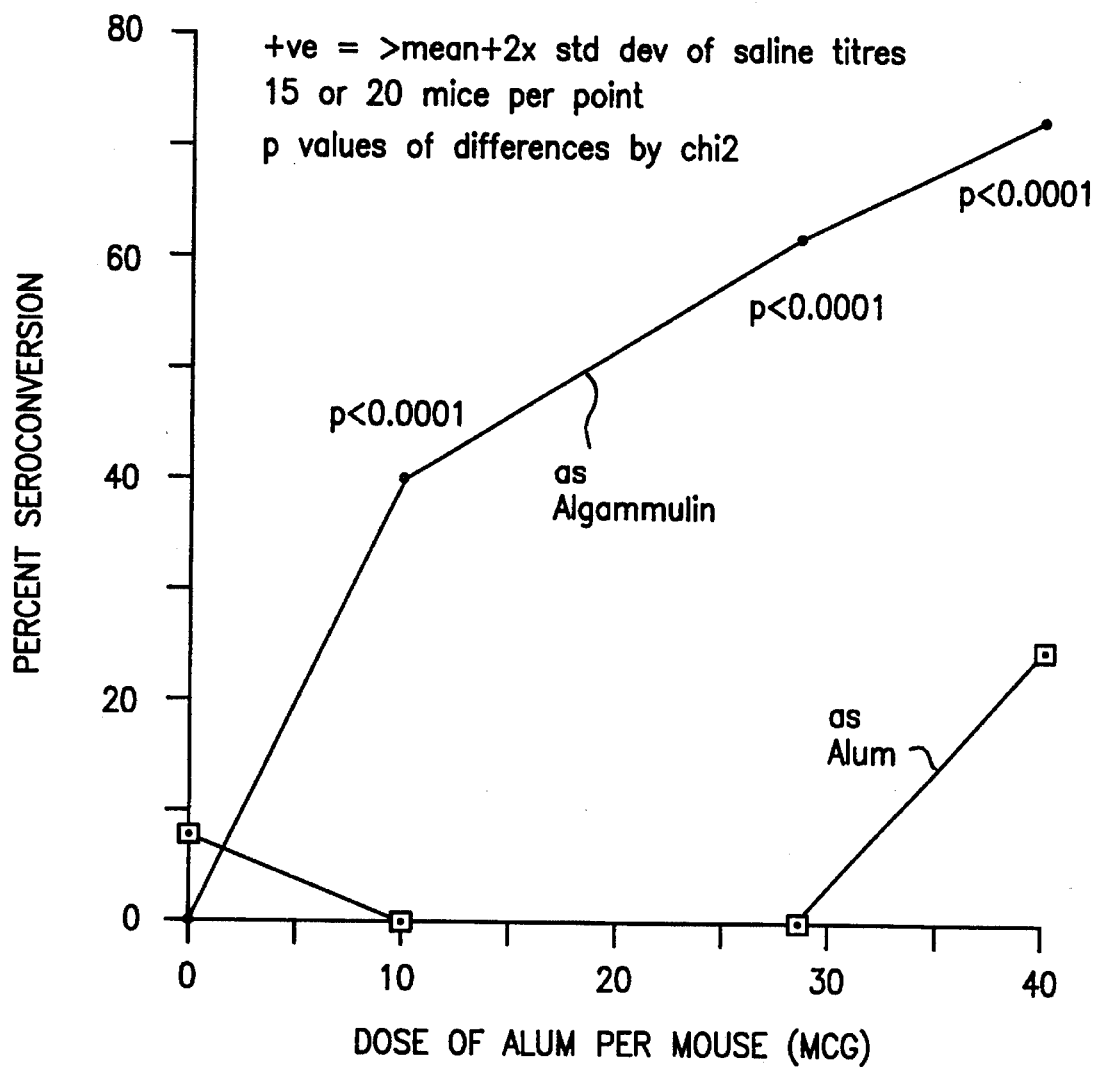
FIG. 4 shows a comparison of the seroconversion enhancement abilities of "Algammaulin".

FIG. 4 shows a seroconversion test, using 15–20 mice per data point and with a protocol similar to that of Example 4 except that sub-seroconversion doses of KLH were used (0.1 mcg/mouse). These doses of KLH alone or mixed with 200 mcg/mouse of gamma inulin only show a seroconversion-positive response (i.e. produce a specific serum antibody titre in excess of the mean plus 2 standard deviations of the mean of the KLH-alone group) in 10% or less of the individual sera. Such positive seroconversion responses were not obtained from KLH on alum until the alum dose reached 40 mcg/mouse. However, highly significant positive seroconversion responses were reached at 10 mcg of alum/mouse provided that the alum was conjugated with gamma inulin as Algammulin, again demonstrating the synergistic effect of conjugation.

Those skilled in the art will realise that many modifications may be made to the compositions and techniques described in this specification without departing from the spirit or scope of the invention.

I claim:

1. An immunoadjuvant composition containing particles wherein said particles comprise inulin or an inulin derivative in the gamma polymorphic form in the same particle with an antigen-binding carrier material.

2. The immunoadjuvant composition according to claim 1, wherein said antigen-binding carrier material is a material of low solubility capable of binding proteinaceous, lipid, carbohydrate or other antigenic substances.

3. The immunoadjuvant composition according to claim 1, wherein said inulin or inulin derivative has a low solubility in aqueous media above 37° C.

4. The immunoadjuvant composition according to claim 1, wherein said inulin derivative is β-D-[ 2-1]polyfructose, or inulin in which the free hydroxy groups have been etherified, or inulin in which the free hydroxyl groups have been esterified.

5. The immunoadjuvant composition according to claim 1, wherein said inulin or inulin derivative in the gamma polymorphic form is co-crystallized in the same particles with the antigen-binding carrier material.

6. The immunoadjuvant composition according to claim 1, wherein said antigen-binding carrier material is a metal-containing precipitate.

7. The immunoadjuvant composition according to claim 6, wherein the metal-containing precipitate is a phosphate, sulphate, hydroxide or hydrate of magnesium, calcium or aluminum.

8. The immunoadjuvant composition according to claim 7, wherein said antigen-binding carrier material is aluminum hydroxide gel.

9. The immunoadjuvant composition according to claim 1, wherein said antigen-binding carrier material is an organic base.

10. The immunoadjuvant composition according to claim 9, wherein the organic base is chitin or a deacetylated derivative thereof or a basic cellulose derivative.

11. The immunoadjuvant composition according to claim 1, wherein said antigen-binding carrier material is an organic acid.

12. The immunoadjuvant composition according to claim 11, wherein the organic acid is a sulphated or phosphorylated polysaccharide or a cellulose derivative.

13. The immunoadjuvant composition according to claim 11, wherein the organic: acid is heparin or dextran.

14. The immunoadjuvant composition according to claim 1, wherein said inulin or inulin derivative has a molecular weight greater than 3000.

15. The immunoadjuvant composition according to claim 14, wherein said inulin or inulin derivative has a molecular weight greater than 8000.

16. The immunoadjuvant composition according to claim 1, comprising particles wherein the gamma inulin has a molecular weight in the range of from about 8000 to about 16000 and is virtually insoluble in water at 37° C.

17. The immunoadjuvant composition according to claim 16, wherein said antigen-binding carrier material is aluminum hydroxide gel.

18. The immunoadjuvant composition according to claim 17, wherein said particles are in the form of a stable suspension of particles which are 50–2000 nanometers in diameter.

19. A process for the preparation of a composition according to claim 1, which comprises the steps of:

providing a suspension of said antigen-binding carrier material, and
  (i) admixing said suspension with inulin or an inulin derivative, and thereafter converting said inulin or inulin derivative to the gamma polymorphic form, or
  (ii) admixing said suspension with inulin or an inulin derivative in gamma polymorphic form;

to effect formation of said inulin or inulin derivatives; in the gamma polymorphic form with said antigen-binding carrier material in the same particle.

20. A process for the preparation of a composition according to claim 1, which comprises the steps of:

(a) recrystallizing crude inulin from an aqueous solution in the presence of a suspension of the carrier material at a temperature substantially below 37° C. to obtain finely divided particles in suspension;

(b) heating said suspension at a temperature in the range of from about 25° to 45° C. for approximately 1 to 3 days;

(c) optionally further heating said suspension at a temperature in the range of from about 40° to 55° C. for approximately 0.5 to 1.5 hours; and (d) isolating the thus-formed gamma inulin/carrier material co-crystallized particles from the suspension.

21. The process according to claim 20, which comprises the further step of:

(e) treating a suspension of the gamma inulin/carrier material particles with an ultrasonic disruption device in order to decrease the particle diameters to an appropriate size range.

22. A process for the preparation of a composition according to claim 1, which comprises the steps of:

(a) recrystallizing crude inulin from an aqueous solution in the presence of a suspension of the carrier material at a temperature in the range of from about 25° to 45° C. to obtain particles in suspension;

(b) optionally further heating said suspension at a temperature in the range of from about 40° to 55° C. for approximately 0.5 to 1.5 hours; and (c) isolating the thus-formed gamma inulin/carrier material co-crystallized particles from the suspension.

23. The process according to claim 22, which comprises the further step of:

(d) treating a suspension of the gamma inulin/carrier material particles with an ultrasonic disruption device in order to decrease the particle diameters to an appropriate size range.

24. A method for the activation of the alternative pathway of complement in a human or animal body, which comprises administering to the human or animal body an effective amount for said activation of an immunotherapeutic preparation which comprises as an active component thereof particles containing inulin or an inulin derivative in gamma polymorphic form in the same particle with an antigen-binding carrier material;

and a pharmaceutically acceptable carrier or diluent.

25. The method according to claim 24 wherein the antigen-binding carrier material is aluminum hydroxide gel.

26. A method for the treatment of an infection by a bacterium, mycoplasma, fungus, virus, protozoan or other microbe, or of an infestation by a worm or parasite, in a human or animal body which comprises administering to the human or animal body an effective amount of an immunotherapeutic preparation which comprises as an active component thereof particles containing inulin or an inulin derivative in gamma polymorphic form in the same particle with an antigen-binding carrier material; and a pharmaceutically acceptable carrier or diluent.

27. The method according to claim 26 wherein the antigen-binding carrier material is aluminum hydroxide gel.

28. A method for the treatment of an infection by a bacterium, mycoplasma, fungus, virus, protozoan or other microbe, or of an infestation by a worm or parasite, in a human or animal body which comprises administering to the human or animal body an effective amount of a vaccine composition comprising particles containing inulin or an inulin derivative in the gamma polymorphic form in the same particle with an antigen-binding carrier material, and one or more antigens adsorbed thereon, together with a pharmaceutically acceptable carrier or diluent.

29. The method according to claim 28 wherein the antigen-binding carrier material is aluminum hydroxide gel.

30. A method for enhancement of an immune response in a human or animal body to which has been administered an immune modulator which comprises administering to the human or animal body an effective amount for enhancement of an immunotherapeutic preparation which comprises as an active component thereof particles containing inulin or an inulin derivative in gamma polymorphic form in the same particle with an antigen-binding carrier material; and a pharmaceutically acceptable carrier or diluent.

31. The method according to claim 30 wherein the antigen-binding carrier material is aluminum hydroxide gel.

* * * * *